US006191256B1

(12) United States Patent
Chen et al.

(10) Patent No.: US 6,191,256 B1
(45) Date of Patent: Feb. 20, 2001

(54) RECOMBINANT FACTOR VIII BINDING PEPTIDES

(75) Inventors: Li Ang Chen, Waverly, TN (US); Joseph A. Buettner; Ruben G. Carbonell, both of Raleigh, NC (US)

(73) Assignee: Bayer Corporation, Berkeley, CA (US)

( * ) Notice: Under 35 U.S.C. 154(b), the term of this patent shall be extended for 0 days.

(21) Appl. No.: 09/196,934

(22) Filed: Nov. 20, 1998

(51) Int. Cl.$^7$ ........................................ C07K 5/00
(52) U.S. Cl. ................ 530/329; 530/330; 530/383; 530/413
(58) Field of Search .................... 530/329, 330, 530/383, 413

(56) References Cited

U.S. PATENT DOCUMENTS 4,518,584 * 5/1985 Mark et al. .......................... 424/858
4,913,902 * 4/1990 Kilpatrick et al. .................. 424/858

FOREIGN PATENT DOCUMENTS

WO 93/00365 * 1/1993 (WO) .

OTHER PUBLICATIONS

Necina et al., *Journal of Chromatography B,* vol. 715, pp. 191–201, 1998.*
Mazo et al., *Proc. Natl. Acad. Sci. USA,* vol. 87, pp. 2112–2116, Mar. 1990.*
Kunst et al., *Nature,* vol. 390, pp. 249–256, Nov. 20, 1997.*
Fleischmann et al., *Science,* vol. 269, pp. 496–512, Jul. 28, 1995.*
Loeber et al., *Biochem. J.,* vol. 304, pp. 687–692, 1994.*
Klenk et al., *Nature,* vol. 390, pp. 364–370, Nov. 27, 1997.*
Necina et al., *Journal of Chromatography B,* vol. 715, pp. 191–201, 1998.*

* cited by examiner

*Primary Examiner*—Christopher S. F. Low
*Assistant Examiner*—Abdel A. Mohamed
(74) *Attorney, Agent, or Firm*—Michael J. Beck; James A. Giblin

(57) ABSTRACT

Peptides that have domains that bind to recombinant factor VIII (rFVIII) are disclosed. A method of rFVIII binding assay using the peptides deduced from a combinatorial library in a filtration plate process is described. A method of using peptides having these available binding domains in an affinity chromatography process to purify factor VIII is also taught.

3 Claims, No Drawings

SEQUENCE LISTING

```
<160> NUMBER OF SEQ ID NOS: 22

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 1

Lys Pro Asn Pro Leu Ala
  1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 2

Arg Asn Pro Pro Asn Asn
  1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 3

Tyr Val Gln Gly Leu Trp
  1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 4

Phe Arg Pro His Trp Ala
  1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 5
```

```
Leu Asn Trp Lys Tyr Gly
  1               5
```

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 6

```
His Tyr Trp Phe Tyr Lys
  1               5
```

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 7

```
Ile Arg Phe Tyr Ser Glu
  1               5
```

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence:Synthetic

<400> SEQUENCE: 8

```
Arg Pro Arg Trp
  1
```

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 9

```
Phe Ala Leu Pro Gly Arg
  1               5
```

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 10

```
Ala Phe Val Arg Ser Leu
  1               5
```

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 11

Asn Ala Ile Phe Gln Trp
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 12

Gln Arg Leu Ile Gln Phe
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 13

Lys Ala Gln Glu Thr Trp
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 14

Glu Pro Arg Val Ile Gly
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 15

Val Tyr Gly Val Gly Gly
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 16

Trp Arg Arg His Arg Tyr
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 17

Phe Tyr Arg Phe Trp Asn

-continued

```
  1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 18

Trp Leu Trp Ser His Asn
  1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 19

Phe His Phe Gly Leu Gln
  1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 20

Trp His His His Arg Gly
  1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 21

His Phe Gln Ile Phe Gly
  1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 22

Phe Val Phe Leu Val Arg
  1               5
```

RECOMBINANT FACTOR VIII BINDING PEPTIDES

BACKGROUND OF THE INVENTION

1. Field

This invention is concerned generally with identifying protein-ligand interactions, and specifically with peptide ligands which bind rFVIII and which may be used in a method for the affinity purification of rFVIII.

2. Prior Art

Human Factor VIII, (antihemophilic factor) is a human plasma protein consisting of 2 polypeptides (light chain molecular weight of 80,000 and heavy chain molecular weight variable from 90,000 to 220,000). It is an essential cofactor in the coagulation pathway; required for the conversion of Factor X into its active form (Factor Xa). Factor VIII circulates in plasma as a non-covalent complex with von Willebrand Factor. Blood concentrations of Factor VIII below 20% of normal cause a bleeding disorder designated hemophilia A. Factor VIII blood levels less than 1% of normal result in a severe bleeding disorder, with spontaneous joint bleeding being the most common symptom. Recombinant DNA technology has allowed construction of plasmids that direct the expression of fusion products of Factor VIII protein in transfected mammalian cells. Factor VIII can be isolated from either a plasma derived source (cryoprecipitate) or from a genetically engineered recombinant source. The term Factor VIII is not meant to be a limitation but refers to a functional protein for treating bleeding disorders.

Several methods have been described for purification of Factor VIII from plasma sources (1,2,3). Several purification schemes utilize antibody affinity columns (4,5). To date, the most successful purifications of Factor VIII from plasma or from recombinant sources has been accomplished by using murine monoclonal antibodies specific to either Factor VIII or von Willibrand Factor.

Although monoclonal antibodies have been used successfully to obtain a relatively pure Factor VIII preparation, monoclonal antibodies can be present in the Factor VIII effluent because of leaching from the support matrix. This raises the possibility of antigenicity when the final preparation is introduced into animal systems, since murine monoclonal antibodies have been shown to be antigenic. A second disadvantage of the use of monoclonal antibodies is the requirement of cell culture facilities for producing the antibodies and the concomitant cost of purification and attachment onto a support matrix. Finally, the stability of the antibody binding site may not be amenable to the rigorous conditions necessary to sanitize the column.

Affinity chromatography is one of the most efficient techniques for purifying a protein from a complex mixture. With potential advantages including high stability, efficiency, selectivity, and low price, peptides have been investigated as affinity ligands in the pharmaceutical industry. A recent approach for identifying such ligands is to screen peptides from combinatorial peptide libraries (6,7,8, 9).

Using the 'divide-couple-recombine' approach (10,11, 12), millions of unique peptides of a defined length may be synthesized on resin beads. Each bead contains a unique peptide sequence. These library beads and their corresponding peptide sequences are then exposed to a target protein. Among these millions of peptide sequences, the target protein may bind to several unique bead-sequences. Those beads and their corresponding sequences must be detected, isolated, and identified. Several detection systems, including calorimetric two-step methods (7,12,13) as well as direct fluorescence detection methods (14,15,16) have been used.

Peptides disclosed in the U.S. patent application Ser. No. 08/595,718, incorporated herein by reference, also were found to bind Factor VIII. See also Necina et al. (23)

SUMMARY OF THE INVENTION

We have now discovered a group of peptides characterized by their ability to bind rFVIII. The sequences of the more preferred peptides having available rFVIII binding domains are Asn-Ala-Ile-Phe-Gln-Trp (SEQ ID NO:11), Ala-Phe-Val-Arg-Ser-Leu (SEQ ID NO:10), Gln-Arg-Leu-Ile-Gln-Phe (SEQ ID NO:12), Phe-Arg-Pro-His-Trp-Ala (SEQ ID NO:4), Arg-Pro-Arg-Trp (SEQ ID NO:8), and others of those presented in Table 1. A

TABLE 1 rFVIII Binding Peptide Sequences
Sequences discovered from screening of hexameric peptide library using
$^{14}$C-rFVIII with confirmed binding of rFVIII.

| Seq ID | | | | | | |
|---|---|---|---|---|---|---|
| 1 | Lys | Pro | Asn | Pro | Leu | Ala |
| 2 | Arg | Asn | Pro | Pro | Asn | Asn |
| 3 | Tyr | Val | Gln | Gly | Leu | Trp |
| 4 | Phe | Arg | Pro | His | Trp | Ala |
| 5 | Leu | Asn | Trp | Lys | Tyr | Gly |
| 6 | His | Tyr | Trp | Phe | Tyr | Lys |
| 7 | Ile | Arg | Phe | Tyr | Ser | Glu |
| 8 | Arg | Pro | Arg | Trp | | |
| 9 | Phe | Ala | Leu | Pro | Gly | Arg |
| 10 | Ala | Phe | Val | Arg | Ser | Leu |
| 11 | Asn | Ala | Ile | Phe | Gln | Trp |
| 12 | Gln | Arg | Leu | Ile | Gln | Phe |
| 13 | Lys | Ala | Gln | Glu | Thr | Trp |
| 14 | Glu | Pro | Arg | Val | Ile | Gly |
| 15 | Val | Tyr | Gly | Val | Gly | Gly |
| 16 | Trp | Arg | Arg | His | Arg | Tyr |
| 17 | Phe | Tyr | Arg | Phe | Trp | Asn |
| 18 | Trp | Leu | Trp | Ser | His | Asn |
| 19 | Phe | His | Phe | Gly | Leu | Gln |
| 20 | Trp | His | His | His | Arg | Gly |
| 21 | His | Phe | Gln | Ile | Phe | Gly |
| 22 | Phe | Val | Phe | Leu | Val | Arg | method of rFVIII binding assay using the peptides deduced from a combinatorial library in a filtration plate process is described. We also describe a method of using the peptides in an affinity chromatography process to purify rFVIII. The method comprises passing a rFVIII containing solution over a substrate which has bound thereupon peptides disclosed herein, and then eluting the rFVIII.

As used herein, an available rFVIII binding domain means a peptide sequence that is sterically available to bind with rFVIII in the surrounding solution and which adopts a conformation that ligates rFVIII with moderate to strong avidity under controlled conditions of pH, ionic strength, and solvent composition. The affinity of binding may be increased or decreased by altering the amino acids adjacent to the above listed sequences. The avidity may be modified further by altering the above mentioned conditions of solvent composition and temperature.

The peptides were isolated and identified using a modified version of a radiological screening technique (17,18,19). We also describe a method of rFVIII binding assay using the identified peptides in a filtration plate format, wherein the method comprises incubating a $^{14}$C-rFVIII containing solution over a substrate that has bound thereupon peptides disclosed herein, and then washing the substrates with appropriate buffer conditions. Finally, a method of rFVIII binding assay using the identified peptides in a column format is also described, wherein the method comprises passing a rFVIII containing solution over a substrate that has bound thereupon peptides disclosed herein, and then eluting the rFVIII with appropriate buffer conditions. Ultimately, this method leads to an affinity chromatography process to purify rFVIII by adopting appropriate elution conditions.

SPECIFIC EMBODIMENTS

Materials

Purified rFVIII (at 500 IU/vial and DOGENATE rFVIII Kogenate at 591 IU/vial of rFVIII in 5–10 mg/mL hSA), ultrafiltered tissue culture fluid containing expressed FVIII (UF-TCF), and tissue culture fluid containing expressed FVIII which had been contacted with a DEAE-Sepharose column resulting in a DEAE concentrate (DEAE eluate) were manufactured by the Bayer Corporation (Berkeley, Calif.). Human serum albumin (hSA) and plasma protein feed (PPF) were also from the Bayer Corporation (Clayton, N.C.). SUPERBLOCK® blocking buffer, Blocker® blot to nonfat powdered milk solution (5% w/v) and BLOCKER casein in Tris buffered saline (TBS) were from Pierce (Rockford, Ill.). Fmoc amino acids were from Novabiochem (San Diego, Calif.). Radiolabeled $^{14}$C-formaldehyde was from NEN Life Science Products (Boston, Mass.). A-arose was from BioRad (Hercules, Calif.). All other chemicals were reagent grade or better.

General Methods

Peptides and a 6-mer combinatorial library were synthesized on TOYOPEARL AF amino 650 M (TosoHaas, Montgomeryville, Pa.) using standard Fmoc chemistry as described (7). Peptides were synthesized robotically with a Gilson AMS 422 (Middleton, Wis.). Peptide densities achieved with the above scheme were typically at 0.1 mmole/g resin. To control the peptide density, a mixture of 1:10 of Fmoc-L-Alanine to tBoc-L-Alanine was used as described (22).

Peptides were re-synthesized directly onto the TOYOPEARL AF amino 650 M resin, at a final substitution density of 0.1 mmole/g resin.

Analvtical Methods

Immunoassay on rFVIII using a sandwich capture ELISA for the light chain and activity assay using a chromogenic substrate (COATEST Factor VIII kit from diaPharma, Franklin, Ohio) were performed on a BIOMEK® automated liquid handling system from Beckman Instruments (Brea, Calif.). The monoclonal antibody for rFVIII light chain (known as C7F7), the ELISA assay standard (lot A70K019), and the control for the activity assay (lot A70A001 @ 140 IU/mL) were from the Bayer Corporation (Berkeley, Calif.). The standard for the activity assay was at 11.2 IU/mL (Bayer, Clayton, N.C.), calibrated against the MEGA 1 standard, which is a working standard used by American manufacturers for measuring factor VIII activity (21).

Peptide densities were determined by quantitative amino acid analysis performed at Commonwealth Biotechnologies, Inc., Richmond, Va., using a Hewlett Packard AMINO QUANT Chemistry system.

Discovery of Binding Peptides To rFVIII

An assay similar to the one described by Mondorf et al. (19) was used to deduce peptides that bind rFVIII. A 6-mer combinatorial peptide library was synthesized directly onto a TosoHaas chromatography resin, TOYOPEARL AF amino 650M, at a final substitution density of 0.1 mmole/g resin. The library was synthesized using Fmoc chemistry with 18 of the 20 natural amino acids (excepting cysteine and methionine).

Sequence identification utilized a radiological detection approach. Radiolabeling of rFVIII was performed at 5° C. by reductive methylation utilizing sodium cyanoborohydride and $^{14}$C-formaldehyde as described (20). The labeling resulted in radioactivity yields ranging from 2 to $57 \times 10^{14}$ dpm/mole rFVIII.

Aliquots of library beads were placed in a reaction column (BioRad, Hercules, Calif.). To prevent nonspecific interactions between peptide and $^{14}$C-rFVIII, the library beads were first incubated with a blocking solution containing SUPERBLOCK blocking buffer, BLOCKER blot to nonfat powdered milk solution (5% w/v) or VLOCKER casein in TBS, followed by PPF in equilibration buffer (20 mM imidazole, 10 mM CaCl2, 0.105 M NaCl, pH 6.9) for 1 hour each, on a rotating plate at ambient temperature. Radiolabeled $^{14}$C-rFVIII at a final concentration of 60 nM in a mixture of PPF, blocking solution and UF-TCF or DEAE eluate was then added to the preblocked library beads and incubated for 2 hours on the rotating plate at 5° C.

After completion of blocking and binding, the beads were rinsed in the reaction column with equilibration buffer, until radioactivity count went down to background level. After rinsing, the beads were transferred to a container by adding low-melt agarose solution (1% by weight), and the slurry poured onto 8×"8" sheets of GENBOND film (FMC, Rockland, Me.). To minimize the loss of beads, the reaction column and the transferring container were rinsed a second time with low melt agarose gel, and this gel was also plated out. The agarose gels were air-dried and exposed to photographic films (HYPERFILM βmax autoradiography film, Amersham Life Science, Arlington Heights, Ill.). After 5 days exposure at room temperature, the films were developed. The background level was extremely low. Re-exposure of the gels for additional 15 days resulted in confirmation of the signals. Careful alignment of the films and the agarose gels allowed for identification of positive beads which were isolated. From the signals, beads were excised, sonicated under heating to free the beads from agarose residues, and sequenced by Edman degradation. The sequence analysis was performed at the Texas A&M University, College Station, Tex., using a Hewlett Packard G1005A Protein Sequencer.

Table 2 lists the screening experiments performed using the above described protocol with variations in the type of blocking agent used (SUPERBLOCK blocking buffer, BLOCKER blot to nonfat powdered milk solution (5% w/v) or BLOCKER casein in TBS), concentration of PPF in the further blocking step, type of feed stream used (UF-TCF or DEAE eluate), amount of library beads used in each experiment, operating temperature, additional washes with 2 M NaCl, pH 6, pH 8, and 1 M $CaCl_2$, and the number of beads selected from each experiment. A total of 62 beads were isolated from the experiments listed in Table 2. Among these, 30 were sequenced by Edman degradation, resynthesized on TOYOPEARL AF amino 650 M resin, and their capacity for binding of rFVIII studied in the confirmatory binding assays.

Twenty-two of the peptide sequences are listed in Table 1. Several consistencies are noted in these sequences. There are three types of residues found in all the sequences: 1) positively-charged residues (Arg, His, Lys); 2) aromatic residues (Tyr, Phe, Trp); and, 3) hydrophobic residues (Ile, Leu, Val, Pro).

Binding Confirmation

Confirmatory binding assays were performed in a filtration plate format using individual peptide sequences synthesized directly onto the TOYOPEARL AF amino 650 M resin, at a final substitution density of 0.1 mmole/g resin. A slurry of each individual peptide sequence was prepared using deionized water. A 100 µL volume of beads (corresponding to 5 mg) was loaded into each well of the filtration plate (MULTISCREEN Assay System, Millipore, Bedford, Mass.), in triplicate for each peptide sequence. Beads were washed with 20% ethanol and incubated overnight with equilibration buffer (20 mM imidazole, 10 mM

TABLE 2

Primary screening experiments leading to discovery of the binding peptides to rFVIII.

| | Blocker | Feed Stream (FS) | Peptide Library used | Comments | N# beads |
|---|---|---|---|---|---|
| Exp 18a | SUPER-BLOCKER (SB) | DEAE eluate, SB, $^{14}$C-rFVII | 6 mg | T = amb (for blocker) T = 5 C | 3 |
| Exp 21 | blotto, casein, | UF-TCF, casein, | 100 mg | (for FS) | 6 |
| Exp 22 | 1:5 PPF | $^{14}$C-rFVIII | 100 mg | | 9 |
| Exp 23 | casein, 1:10 PPF | DEAE eluate, SB, $^{14}$C-rFVII | 100 mg | | 1 |
| Exp 24 | | | 100 mg | T = amb | 7 |
| Exp 25 | | UF-TCF, $^{14}$C-rFVIII | 200 mg | extremes added: 2M NaCl, pH6, pH8, 1M CaCl$_2$ T = 5 C | 32 not sequenced |
| Exp 26 | | DEAE eluate, $^{14}$C-rFVIII | 200 mg | | 4 |

CaCl$_2$, 0.105 M NaCl, pH 6.9). A 100 µL aliquot of $^{14}$C-rFVIII diluted in neat PPF to a final concentration of 20–30 nM was loaded into each well and incubated for 1 hour at 5° C. Filtrate (unbound $^{14}$C-rFVIII) was collected into a microtiter plate and transferred to liquid scintillation vials for dpm counting. Beads were washed sequentially with: 100 µL of equilibration buffer for 15 minutes, 200 µL of 0.5 M CaCl$_2$ (in equilibration buffer), 200 µL of 1.0 M CaCl$_2$ (in equilibration buffer), and 200 uL of 2% by volume glacial acetic acid in water, for 1 hour each at 5° C. Scintillation counting on the unbound $^{14}$C-rFVIII (plus equilibration buffer wash), salt and acid washes, as well as on the beads was then performed and the overall mass balance calculated.

Performance of the rFVIII Binding Peptides

Additional confirmatory binding assay and performance of the discovered binding peptides in terms of total rFVIII and activity recovery was performed in a column chromatographic format on a microbore HPLC. The resins were packed into 0.4×5 cm columns (Thomson, Springfield, Va.) and tested on the MICHROM HPLC system (Michrom BioResources, Auburn, Calif.). The elution program for the trials utilized the following method. The column was pre-equilibrated with equilibration buffer (as above). A 1 mL aliquot of 1:10 PPF followed by 1 mL of rFVIII (10,000 ng) in 1:10 PPF were injected and allowed sufficient time to flow through the column using equilibration buffer. The column was then washed with step elutions of 0.5 M and 1.0 M CaCl$_2$ in equilibration buffer. The column was exposed to equilibration buffer. Remaining protein was eluted with 2% by volume glacial acetic acid in water. Columns were kept at 5° C. during the chromatographic runs. For each 1 mL injection (equilibration buffer, 1:10 PPF and 10,000 ng rFVIII in 1:10 PPF), the chromatographic cycle was run for 45 minutes (injection, flow through, 0.5 M CaCl$_2$, 1.0 M CaCl$_2$, equilibration buffer, 2% acetic acid, equilibration buffer).

A Gilson FC204 fraction collector at the HPLC outlet collected individual eluates for further analysis. Each collection tube had 100 µL hSA added to it to stabilize the rFVIII. Fractions collected from the 2% acetic acid eluates were neutralized with 2 M Tris, pH 10.5 to bring the pH to neutrality. The fractions were analyzed for total protein by the integration of the absorbance at 280 nm, for rFVIII by immunoassay (sandwich capture ELISA), and for rFVIII activity by a chromogenic substrate assay.

Results

Tables 3 and 4 present the results from the confirmatory binding assays using the plate format. Beads presenting the appropriate peptide sequence on the surface were placed in the filtration plate wells and incubated sequentially with equilibration buffer, $^{14}$C-rFVIII in PPF, equilibration buffer, 0.5 M CaCl$_2$ wash, 1.0 M CaCl$_2$ wash and 2% acetic acid wash. After each incubation, filtrate was collected in microtiter plates, and dpm counted on each

TABLE 3

Confirmation of binding for peptide sequences 1 to 8 and 16 to 18 using $^{14}$C-rFVIII in the plate format binding assay. Sequences 1 to 8 resulted in $^{14}$C-rFVIII eluted in the 0.5M CaCl$_2$ wash while sequences 16 to 18 in the 2% acetic acid wash. Binding results from a non binder sequence IGF are included for comparison, as well as the results from the control ($^{14}$C-rFVIII loaded into wells without beads). 100 µL of $^{14}$C-rFVIII at 20 nM and 3.0 × 10$^{15}$ DPM/mole were loaded into each well containing 5 mg beads.

| Seq. ID | Sequence | 0.5M CaCl2 dpm | % total | 2% acetic acid dpm | % total | beads dpm | % total | Total dpm |
|---|---|---|---|---|---|---|---|---|
| 1 | KPNPLA | 2694 | 85 | 368 | 12 | 99 | 3 | 3162 |
| 2 | RNPPNN | 2366 | 86 | 322 | 12 | 79 | 3 | 2767 |
| 3 | YVQGLW | 1502 | 74 | 379 | 19 | 140 | 7 | 2020 |
| 4 | FRPHWA | 2905 | 78 | 631 | 17 | 209 | 6 | 3744 |
| 5 | LNWKYG | 3519 | 86 | 430 | 10 | 143 | 3 | 4091 |
| 6 | HYWFYK | 3236 | 83 | 458 | 12 | 187 | 5 | 3881 |
| 7 | IRFYSE | 3184 | 85 | 415 | 11 | 165 | 4 | 3764 |
| 8 | RPRW | 3543 | 86 | 377 | 9 | 178 | 4 | 4098 |
| 16 | WRRHRY | 608 | 21 | 1302 | 45 | 986 | 34 | 2897 |
| 17 | FYRFWN | 498 | 17 | 2156 | 72 | 355 | 12 | 3009 |
| 18 | WLWSHN | 651 | 25 | 1752 | 67 | 205 | 8 | 2608 |
| | IGF | 219 | 80 | 41 | 15 | 14 | 5 | 274 |
| control | no beads | 98 | 86 | 16 | 14 | | 0 | 114 | filtrate sample. Sequences 1 to 8 (Table 3) and 9 to 15 (Table 4) resulted in high percentage $^{14}$C-rFVIII bound and eluted in 0.5 M CaCl$_2$, ranging from 48 to 95% eluted by the salt wash. Sequences 16 to 18 (Table 3) and 19 to 21 (Table 4) resulted in most of the bound rFVIII (from 45 to 72%) eluted by the 2% acetic acid wash. Finally, sequence 22 resulted in tight binding, with 65% of the bound $^{14}$C-rFVIII still on the peptide bead after salt and acid washes. Results for a non-binding peptide sequence (IGF), as well as for the control with no beads in the inicrotiter plate wells, are also shown for comparison.

TABLE 4

Confirmation of binding for peptide sequences 9 to 15 and 19 to 22 using $^{14}$C-rFVIII in the plate format binding assay. Sequences 9 to 15 resulted in $^{14}$C-rFVIII eluted in the 0.5M CaCl$_2$ wash while sequences 19 to 21 in the 2% acetic acid wash. Sequence 22 is a tight binder, not eluting the bound $^{14}$C-rFVIII by the salt or acid washes performed. The control ($^{14}$C-rFVIII loaded into wells without beads) is also presented. 100 μL of $^{14}$C-rFVIII at 30 nM and 5.0 × 10$^{15}$ dpm/mole were loaded into each well containing 5 mg beads.

| Seq. ID | Sequence | 0.5M CaCl2 dpm | % total | 2% acetic acid dpm | % total | beads dpm | % total | Total dpm |
|---|---|---|---|---|---|---|---|---|
| 9 | FALPGR | 3414 | 93 | 176 | 5 | 68 | 2 | 3658 |
| 10 | AFVRSL | 3491 | 93 | 188 | 5 | 85 | 2 | 3764 |
| 11 | NAIFQW | 1049 | 48 | 518 | 23 | 641 | 29 | 2208 |
| 12 | QRLIQF | 3191 | 90 | 271 | 8 | 95 | 3 | 3557 |
| 13 | KAQETW | 3884 | 95 | 135 | 3 | 77 | 2 | 4096 |
| 14 | EPRVIG | 1994 | 91 | 130 | 6 | 60 | 3 | 2184 |
| 15 | VYGVGG | 2162 | 93 | 115 | 5 | 53 | 2 | 2330 |
| 19 | FHFGLQ | 457 | 15 | 2148 | 72 | 382 | 13 | 2987 |
| 20 | WHHHRG | 485 | 12 | 2099 | 54 | 1300 | 33 | 3884 |
| 21 | HFQIFG | 722 | 21 | 2208 | 63 | 554 | 16 | 3484 |
| 22 | FVFLVR | 675 | 16 | 783 | 19 | 2658 | 65 | 4116 |
| control | no beads | 98 | 75 | 33 | 25 | | 0 | 131 |

In Table 3, the $^{14}$C-rFVIII was loaded at 20 nM (in PPF) and the radiolabeling yield was at $3.0 \times 10^{15}$ dpm/mole. In Table 4, the $^{14}$C-rFVIII was loaded at 30 nM (in PPF) and the radiolabeling yield was at $5.0 \times 10^{15}$ dpm/mole.

Tables 5 and 6 present the results from the additional confirmatory binding assays using the column format. The chromatography method was run by injecting the samples at a flow rate of 865 μL/min (413 cm/hr). In order to provide a 10 minute residence time of sample in the column the flow was decreased to 17 μL/min (10 cm/hr) upon injection.

TABLE 5

Confirmation of binding for peptide sequences 1 to 8 and 16 to 18 in the column format binding assay. Sequences 1 to 8 resulted in rFVIII eluted in the 0.5M CaCl$_2$ wash while sequences 16 to 18 in the 2% acetic acid wash. Binding results from a non binder sequence IGF are included for comparison, as well as the results from the control (rFVIII injected in the HPLC without any column attached).

| Seq ID | Sequence | Flow through ng | % total | 0.5M CaCl2 ng | % total | 2% acetic acid ng | % total | Total ng |
|---|---|---|---|---|---|---|---|---|
| 1 | KPNPLA | 583 | 10 | 4961 | 88 | 61 | 1 | 5651 |
| 2 | RNPPNN | 447 | 7 | 5745 | 92 | 31 | 0 | 6245 |
| 3 | YVQGLW | n.a. | | n.a. | | n.a. | | n.a. |
| 4 | FRPHWA | 225 | 4 | 5510 | 90 | 160 | 3 | 6123 |
| 5 | LNWKYG | 25 | 0 | 5530 | 97 | 125 | 2 | 5680 |
| 6 | HYWFYK | 105 | 2 | 5658 | 90 | 160 | 3 | 6320 |
| 7 | IRFYSE | 228 | 4 | 5836 | 94 | 77 | 1 | 6225 |
| 8 | RPRW | 122 | 2 | 5449 | 97 | 10 | 0 | 5623 |
| 16 | WRRHRY | 56 | 2 | 338 | 9 | 2550 | 71 | 3615 |
| 17 | FYRFWN | 127 | 3 | 1622 | 37 | 2336 | 54 | 4348 |
| 18 | WLWSHN | 8 | 0 | 2362 | 56 | 760 | 18 | 4200 |
|  | IGF | 4719 | 95 | 201 | 4 | 10 | 0 | 4962 |
| control | no column | 5110 | 98 | 80 | 2 | 10 | 0 | 5212 |

Following the incubation, the flow was set at 865 μL/min (413 cm/hr) for the step elutions of 0.5 M CaCl$_2$, 1.0 M CaCl$_2$, and 2% acetic acid. Results are expressed in terms of the total mass of rFVIII in each fraction, as determined by the sandwich capture ELISA assay for the rFVIII light chain. Sequences 1 to 8 and 18 (Table 5) and 9 to 15 (Table 6) resulted in high percentage of the protein bound and eluted in 0.5 M CaCl$_2$, ranging from 32 to 98% eluted by the salt wash. Sequences 16 to 17 (Table 5) and 19 to 22 (Table 6) resulted in 54 to 100% of the bound rFVIII eluted by the 2% acetic acid wash. A control using a non-binding peptide sequence (IGF) is also shown for comparison—in this case, 95% of the rFVIII loaded to the column was collected in the flow through fraction. Additional controls with no

TABLE 6

Reconfirmation of binding for peptide sequences 9 to 15 and 19 to 22 in the column format binding assay. Sequences 9 to 15 resulted in rFVIII eluted in the 0.5M CaCl$_2$ wash while sequences 19 to 21 in the 2% acetic acid wash. Results for the control (rFVIII injected in the HPLC without column) are also presented for comparison.

| Seq ID | Sequence | Flow through ng | % total | 0.5M CaCl2 ng | % total | 2% acetic acid ng | % total | Total ng |
|---|---|---|---|---|---|---|---|---|
| 9 | FALPGR | 0 | 0 | 7154 | 97 | 181 | 2 | 7403 |
| 10 | AFVRSL | 0 | 0 | 11023 | 98 | 135 | 1 | 11272 |
| 11 | NAIFQW | 639 | 7 | 7481 | 78 | 1069 | 11 | 9641 |
| 12 | QRLIQF | 0 | 0 | 9223 | 96 | 188 | 2 | 9579 |
| 13 | KAQETW | 641 | 7 | 8018 | 90 | 87 | 1 | 8863 |
| 14 | EPRVIG | 5828 | 66 | 2850 | 32 | 75 | 1 | 8851 |
| 15 | VYGVGG | 3572 | 42 | 4611 | 55 | 121 | 1 | 8427 |
| 19 | FHFGLQ | 0 | 0 | 1075 | 25 | 2569 | 60 | 4283 |
| 20 | WHHHRG | 0 | 0 | 36 | 1 | 4719 | 95 | 4966 |
| 21 | HFQIFG | 0 | 0 | 1239 | 22 | 3284 | 60 | 5510 |
| 22 | FVFLVR | 0 | 0 | 4 | 0 | 4500 | 100 | 4504 |
| control | no column | 8109 | 95 | 334 | 4 | 63 | 1 | 8564 | colummns connected to the HPLC system were also run for comparison. Theoretically, 10,000 ng of rFVIII (in 1:10 PPF) were expected to be loaded in each column. In Table 5, the mass balance on the total amount of rFVIII in the no column control showed only about 52% of theroetical value actually loaded in the system. In Table 6, the mass balance on the control resulted in 86% of the theoretical value loaded in the system.

Performance of the rFVIII Binding Peptides

Tables 7 and 8 list the sequences for which activity recovery was determined by a chromogenic substrate assay (COASTEST kit, diaPharma, Franklin, Ohio). Chromatographc conditions are the same as described above for the results from Tables 5 and 6. It can be

TABLE 7

Activity recovery for peptide sequences 1, 2, 5, 6 and 7. The sequences which resulted in rFVIII eluted in the 0.5M CaCl$_2$ showed high activity recovery, ranging from 86 to 96%. Activity recovery for the control (rFVIII injected through the HPLC without column) is also shown for comparison.

| Seq ID | Sequence | Flow through IU | % total | 0.5M CaCl2 IU | % total | 2% acetic acid IU | % total | Total IU |
|---|---|---|---|---|---|---|---|---|
| 1 | KPNPLA | 0.03 | 0 | 32.8 | 90 | 0.58 | 2 | 36.5 |
| 2 | RNPPNN | 0.4 | 1 | 51.6 | 95 | 0.5 | 1 | 54.3 |
| 5 | LNWKYG | 0.0 | 0 | 36.3 | 96 | 1.2 | 3 | 37.8 |
| 6 | HYWFYK | 0.0 | 0 | 59.4 | 86 | 0.5 | 1 | 68.7 |
| 7 | IRFYSE | 0.0 | 0 | 40.6 | 96 | 0.4 | 1 | 42.5 |
| control | no column | 54.8 | 96 | 1.9 | 3 | 0.0 | 0 | 56.9 |

TABLE 8

Activity recovery for peptide sequences 9 to 15 and 19 to 22. The sequences which resulted in rFVIII eluted in the 0.5M CaCl₂ showed high activity recovery, ranging from 25 to 98%. Activity recovery for the sequences that elute rFVIII in the acid fraction is very low. Results for the control (rFVIII injected through the HPLC without column) are also shown for comparison.

| Seq ID | Sequence | Flow through IU | % total | 0.5M CaCl2 IU | % total | 2% acetic acid IU | % total | Total IU |
|---|---|---|---|---|---|---|---|---|
| 9 | FALPGR | 0.0 | 0 | 68.9 | 98 | 0.1 | 0 | 70.2 |
| 10 | AFVRSL | 0.0 | 0 | 53.1 | 98 | 0.1 | 0 | 54.3 |
| 11 | NAIFQW | 2.5 | 4 | 54.4 | 90 | 0.0 | 0 | 60.4 |
| 12 | QRLIQF | 0.0 | 0 | 45.1 | 97 | 0.08 | 0 | 46.6 |
| 13 | KAQETW | 0.8 | 2 | 48.3 | 96 | 0.09 | 0 | 50.3 |
| 14 | EPRVIG | 42.9 | 73 | 14.7 | 25 | 0.00 | 0 | 58.6 |
| 15 | VYGVGG | 17.3 | 38 | 27.2 | 60 | 0.08 | 0 | 45.4 |
| 19 | FHFGLQ | 0.5 | 2 | 9.9 | 51 | 1.4 | 7 | 19.5 |
| 20 | WHHHRG | 0.0 | 0 | 0.4 | 4 | 3.5 | 45 | 7.8 |
| 21 | HFQIFG | 0.0 | 0 | 11.4 | 53 | 4.1 | 19 | 21.2 |
| 22 | FVFLVR | 0.0 | 0 | 0.0 | 0 | 2.3 | 100 | 2.3 |
| control | no column | 37.5 | 92 | 2.6 | 6 | 0.2 | 0 | 40.8 | observed that most of the rFVIII eluted in the salt fraction (0.5 M CaCl₂) showed activity recovery, while for the rFVIII eluted in acid, practically no activity is recovered. Sequences 1, 2, 5, 6, 7, 9, 10, 11, 12, and 13 resulted in high activity recoveries, ranging from 86 to 98%.

Table 9 presents a summary of the performance of the discovered peptide sequences that resulted in binding and elution of the rFVIII in the 0.5 M CaCl₂ fractions (sequences 1 to 15). Chromatographic conditions are the same as described above for the results from Tables 5 and 6. The rFVIII present in these fractions ranged from 32–98% of the total rFVIII

TABLE 9

Performance of the peptide sequences that elute rFVIII in the 0.5M CaCl₂. Peak areas (x106) of the 0.5M CaCl₂ fractions correlated with the percentage total rFVIII and rFVIII activity recovered. Results based on the injection of 10,000 ng rFVIII (in 5 mg PPF) in equilibration buffer at 5° C.

| Seq ID | Sequence | ELISA results ng | % total | Activity results IU | % total | Peak area |
|---|---|---|---|---|---|---|
| 1 | KPNPLA | 4961 | 88 | 32.8 | 90 | 7.7 |
| 2 | RNPPNN | 5745 | 92 | 51.6 | 95 | 5.0 |
| 3 | YVQGLW | n.a. | | n.a. | | n.a. |
| 4 | FRPHWA | 5510 | 90 | n.a. | | 81.9 |
| 5 | LNWKYG | 5530 | 97 | 36.3 | 96 | 3.6 |
| 6 | HYWFYK | 5658 | 90 | 59.4 | 86 | 3.4 |
| 7 | IRFYSE | 5836 | 94 | 40.6 | 96 | 4.2 |
| 8 | RPRW | 5449 | 97 | n.a. | | 18.1 |
| 9 | FALPGR | 7154 | 97 | 68.9 | 98 | 4.9 |
| 10 | AFVRSL | 11023 | 98 | 53.1 | 98 | 22.8 |
| 11 | NAIFQW | 7481 | 78 | 54.4 | 90 | 0.4 |
| 12 | QRLIQF | 9223 | 96 | 45.1 | 97 | 13.7 |
| 13 | KAQETW | 8018 | 90 | 48.3 | 96 | 4.4 |
| 14 | EPRVIG | 2850 | 32 | 14.7 | 25 | 0.0 |
| 15 | VYGVGG | 4611 | 55 | 27.2 | 60 | 2.0 | loaded, and the activity recovery ranged from 25 to 98%. The integrated peak areas (based on absorbance at 280 nm) for the injection of 10,000 ng rFVIII (in 1:10 PPF, with a total protein of approximately 5 mg/mL) at 5° C. are also presented. All the sequences eluted enriched rFVIII in the salt fraction.

CONCLUSION

Peptides sequences with varying degrees of specificity and affinity for factor VIII were identified from the screening of a combinatorial peptide library. A number of sequences including Asn Ala Ile Phe Gln Trp (SEQ ID NO:11) showed the ability to purify factor VIII. The affinity of these peptide sequences for factor VIII may be altered by deleting, substituting, or adding amino acids to the disclosed sequences. It is expected that the binding domains of the disclosed peptide sequences may be contained within other, longer peptides and still bind to factor VIII.

The above examples are intended to illustrate the invention, and it is thought variants will occur to those skilled in the art. Accordingly, it is intended that the scope of the invention should be limited only by the claims below.

REFERENCES

1. Tuddenham, E. G. D., et al., "The properties of factor VIII coagulant activity prepared by immunoadsorbent chromatography", J Lab Clin Med, 93: 40 (1979).
2. Austen, D. E. G., "The chromatographic separation of factor VIII on arninohexyl sepharose", Brit J Heamotol, 43: 669 (1979).
3. Zimmerman, et al., "Ultrapurification of factor VIII using monoclonal antibodies", U.S. Pat. No. 4,361,509 (Nov. 30, 1982).
4. Wood, W. I., et al., Expression of active human factor VIII from recombinant DNA clones", Nature, 312: 330–337 (1984).
5. Rotblat, F., et al., "Purification of human factor VIII:C and its characterization by western blotting using monoclonal antibodies", Biochemistry, 24: 4294 (1985).
6. Baumbach, G. A., et al., "Protein Purification Using Affinity Ligands from Peptide Libraries", BioPharm, May 1992, 24–35.
7. Buettner, J. A., et al., "Chemically derived peptide libaries: A new resin and methodology for lead identification", Int J Peptide Protein Res, 47: 70–83 (1996).
8. Huang, P. Y., et al., "Affinity Purification of Proteins Using Ligands Derived from Peptide Libraries", Biotechnol & Bioeng, 47: 288–297 (1995).
9. Huang, P. Y., et al., "Affinity Purification of von Willebrand Factor Using Ligands Derived from Peptide Libraries", Bioorg & Med Chem, 4: 699–708 (1996).
10. Furka, A., et al., "General method for rapid synthesis of multicomponent peptide mixtures", Int J Peptide Protein Res, 37: 487–493 (1992).
11. Lam, K. S., et al., "A new type of synthetic peptide library for identifying ligand-binding activity", Nature, 354: 82–84 (1991).
12. Houghten, R. A., et al., "Generation and use of synthetic peptide combinatorial libraries for basic research and drug discovery", Nature, 354: 84–86 (1991).
13. Lam, K. S., et al., "Application of a dual color detection scheme in the screening of a random combinatorial peptide library", J Immunol Meth, 180: 219–223 (1995).
14. Meldal, M., et al., "Portion-mixing peptide libraries of quenched fluorogenic substrates for complete subsite mapping of endoprotease specificity", Proc Nat Acad Sci USA, 91: 3314–3318 (1994).
15. Meldal, M., et al., "Direct visualization of enzyme inhibitors using a portion mixing inhibitor library containing a quenched fluorogenic peptide substrate. Part 1. Inhibitors for subtilisin Carlsberg", J. Chem. Soc. Perkin Trans. 1: 1591–1596 (1995).

16. Needels, M. C., et al., "Generation and screening of an oligonucleotide-encoded synthetic peptide library", Proc Nat Acad Sci USA, 90: 10700–10704 (1993).
17. Kassarjian, A., et al., "Screening of Synthetic Peptide Libraries with Radiolabeled Acceptor Molecules", Peptide Research, 6: 129–133 (1993).
18. Turck, C. W., "Radioactive Screening of Synthetic Peptide Libraries", Methods: A Companion to Methods in Enzymology, 6: 396–400 (1994).
19. Mondorf, K, et al., J Pept. Res. in press (1998).
20. Jentoft, N. et al., "Protein Labeling by Reductive Alkylation", Meth Enzymol, 91: 570–579 (1983).
21. Barrowcliffe, T. W., "Recommendations for the assay of high-purity factor VIII concentrates" Thromb Haem 70: 876–877 (1993).
22. Baumbach, G. A., et al., "Peptides which bind to prothrombin and thrombin", U.S. Pat. No. 5,831,003 (Nov. 3, 1998).
23. Necina, R., et al., "Peptide affinity chromatography of human clotting factor VIII: Screening of the vWF-binding domain", J Chrom B 715: 191–201 (1998).

What is claimed is:

1. A composition comprising a peptide having an available rFVIII binding domain, wherein the binding domain is selected from the group consisting of Arg Asn Pro Pro Asn Asn; Tyr Val Gln Gly Leu Trp; Phe Arg Pro His Trp Ala; His Tyr Trp Phe Tyr Lys; Ile Arg Phe Tyr Ser Glu; Asn Ala Ile Phe Gln Trp; Gln Arg Leu Ile Gln Phe; Lys Ala Gln Glu Thr Trp; and Glu Pro Arg Val Ile Gly (SEQ ID NOS: 2–4, 6, 7, and 11–14, respectively).

2. The composition of claim 1, wherein the peptide is immobilized upon a water-insoluble support.

3. The composition of claim 2, wherein the support is a chromatography medium.

* * * * *